United States Patent [19]

Kobayashi et al.

[11] Patent Number: 5,000,945

[45] Date of Patent: Mar. 19, 1991

[54] METHOD OF STABILIZING A UVB ABSORBING COMPOUND, A STABILIZED UV ABSORBER, AND A COSMETIC COMPOSITION CONTAINING THE SAME

[75] Inventors: Toru Kobayashi, Kawasaki; Takeshi Miyoshi; Masahiro Takehara, both of Fujisawa, all of Japan

[73] Assignee: Ajinomoto Co., Inc., Tokyo, Japan

[21] Appl. No.: 242,166

[22] Filed: Sep. 8, 1988

Related U.S. Application Data

[63] Continuation-in-part of Ser. No. 38,364, Apr. 14, 1987, abandoned.

[30] Foreign Application Priority Data

| Apr. 22, 1986 | [JP] | Japan | 61-92481 |
| Oct. 16, 1986 | [JP] | Japan | 61-246308 |
| Oct. 16, 1986 | [JP] | Japan | 61-246309 |
| Nov. 14, 1986 | [JP] | Japan | 61-271287 |
| Sep. 10, 1987 | [JP] | Japan | 62-227394 |

[51] Int. Cl.$^5$ .............. A61K 7/027; A61K 7/06; A61K 7/42; A61K 7/48
[52] U.S. Cl. .............. 424/59; 424/DIG. 1; 424/DIG. 2; 424/47; 424/60; 424/62; 424/63; 424/64; 424/69; 424/70; 424/78; 424/79; 424/80; 424/81; 426/654; 514/844; 514/845; 514/937; 514/938; 514/939; 514/972
[58] Field of Search .................. 424/59, 60

[56] References Cited

U.S. PATENT DOCUMENTS

| 4,264,581 | 4/1981 | Kerkhof et al. | 424/59 |
| 4,710,373 | 12/1987 | Nakamura | 424/59 |

FOREIGN PATENT DOCUMENTS

| 0198397 | 10/1986 | European Pat. Off. | 514/847 |
| 2375867 | 7/1978 | France | 514/844 |
| 2083240 | 3/1982 | United Kingdom | 424/69 |

OTHER PUBLICATIONS

Chemical Abstracts, vol. 56, No. 7, Apr. 1962, abstract No. 7299b, Columbus, Ohio, U.S.; Osamu Shimomura et al., "5-Imidazolone. I. Syntheses and Ultraviolet Absorption Spectra of 1,2,4-Trisubstituted-5-Imidazolones."; Nippon Kagaku Zasshi 81, pp. 1434–1438.
Chemical Abstracts, vol. 57, No. 13, Dec. 1962, col. 16583b, Columbus, Ohio, U.S.; M. Vanghelovici et al.: "Oxazolone Series. IX. The Action of Cyclohexylamine and Ethylenediamine on Oxazolones."; & Stiinte Chim. 8, pp. 249–254.
Chemical Abstracts, vol. 54, No. 9, May 1960, Abstract No. 8788f, Columbus, Ohio, U.S.; Robert Pfleger et al.: "Reactivity of the Methyl Group in 2-Methyl-4-Banzal-5-Imidazoles"; & IBID, pp. 1494–1499.
Chemical Abstracts, vol. 88, No. 3, Jan. 16, 1978, p. 621, col. 2, Abstract No. 22747t, Columbus, Ohio, U.S.; Shalaby et al., "Chemical Reactivity of 2-Thiohydantoin Derivatives"; & Org. Chem. 1977, 32B(8), pp. 948–953.
Chemical Abstracts, vol. 104, No. 7, Feb. 17, 1986, p. 515, col. 2, Abstract No. 50807e, Columbus, Ohio, U.S.; K. Pradeep Triphathy et al.: "A Facile Synthesis of N-Substituted 2-Acylamino-2-Alkenamides"; & Synthesis, 1985 (3), pp. 285–288.
Chemical Abstracts, vol. 103, No. 12, Sep. 23, 1985, p. 310, col. 2, Abstract No. 92707g, Columbus, Ohio, U.S.; Weiqin Liu et al.: "Measurement of Partition Coefficients of Cinnamamide Compounds"; & Beijing Yixueyuan Xuebao, 1983, 15(1), pp. 75–81.
Chemical Abstracts Service Registry Handbook, Number Section 1986 Supplement, p. 963RO, col. 2, Source: U.S. National Library of Medicine.

*Primary Examiner*—Dale R. Ore
*Attorney, Agent, or Firm*—Oblon, Spivak, McClelland, Maier & Neustadt

[57] ABSTRACT

A process for stabilizing a specific UVB absorbing compound which comprises adding to said UVB absorbing compound at least one specific UVA absorbing compound in an amount of 0.1–10 parts by weight based on 1 part by weight of UVB absorbing compound is disclosed and also a cosmetic composition and a UV absorber, both containing said specific UVB absorbing compound and said specific UVA absorbing compound, respectively.

21 Claims, 7 Drawing Sheets

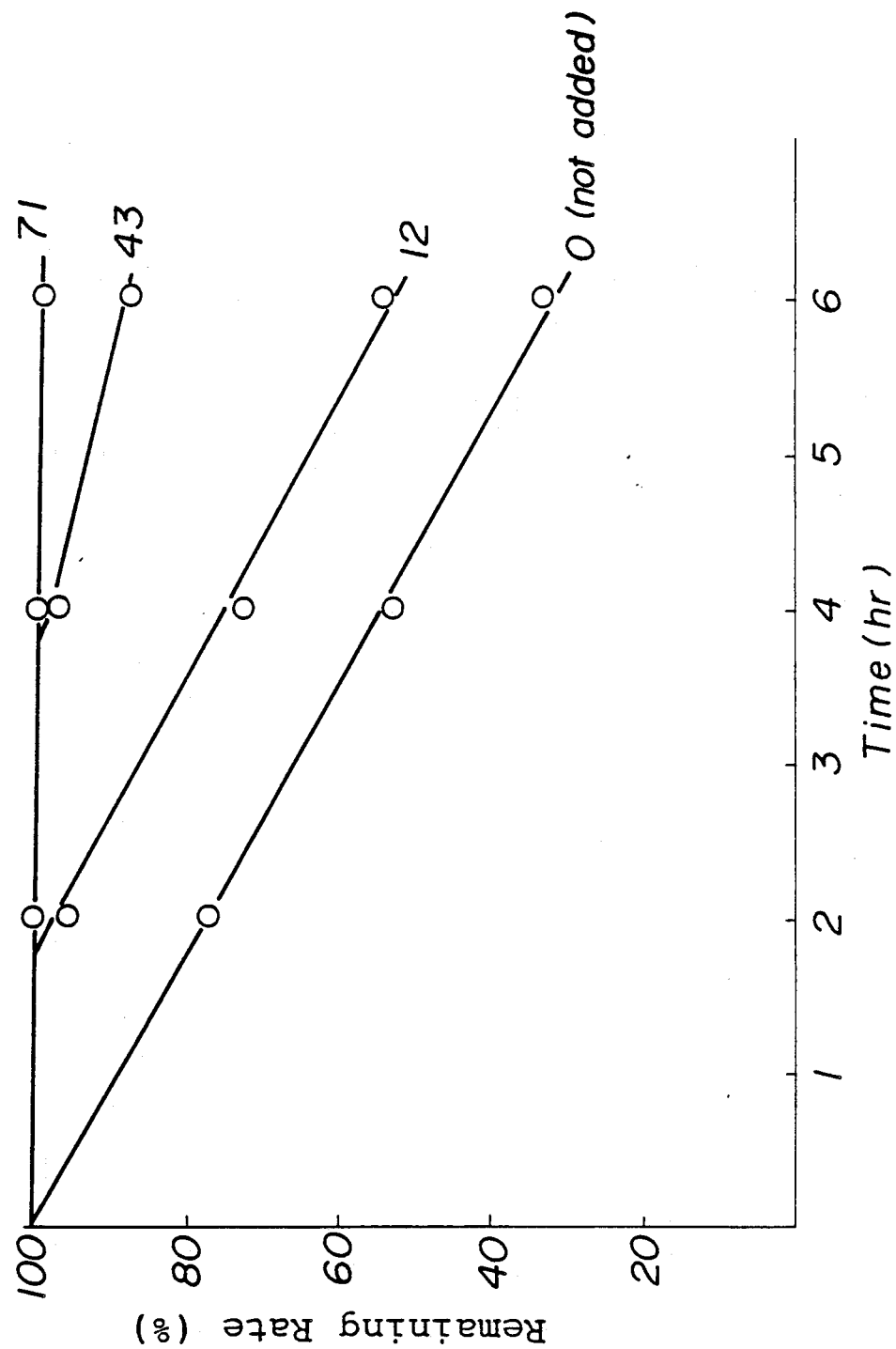

METHOD OF STABILIZING A UVB ABSORBING COMPOUND, A STABILIZED UV ABSORBER, AND A COSMETIC COMPOSITION CONTAINING THE SAME

This application is a continuation-in-part of copending Application Ser. No. 038,364 filed Apr. 14, 1987, now abandoned.

BACKGROUND OF THE INVENTION

Ultraviolet light absorbing compounds are effective in sunburn-preventing cosmetics, in preventing yellowing of fibers, resins, etc. and in protecting containers, packing materials and contents therein from ultraviolet light, and the compounds are used in broad fields such as paints, resins, medicines, foodstuffs and cosmetics.

Since short wavelength ultraviolet light (UVC) having a wavelength of not more than about 290 nm is absorbed by the ozone layer surrounding the earth, the ultraviolet light component of sunlight which influences human skin and industrial products is medium wavelength ultraviolet light (UVB) having a wavelength of 290 to 320 nm and long wavelength ultraviolet light (UVA) having a wavelength of 320 to 400 nm.

Hitherto, a large number of UVB absorbing compounds have been known.

For instance, esters of p-dimethylaminobenzoic acid are the compounds which are used in cosmetics and industrial fields as a UVB absorber and have a structure represented by the following formula (I):

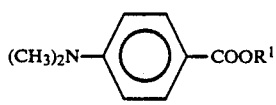

Of the above-mentioned compounds, the compound wherein $R^1$ represents a 2-ethylhexyl group is used as a raw material for cosmetics of broad use in sun-screen agents, etc.

The above-mentioned esters of p-dimethylaminobenzoic acid have been known to be decomposed by light irradiation. See A.E. Mark et al., "Photochemistry and Photobiology", 5, 533–542(1966).

It has been known that the esters of p-dimethylaminobenzoic acid are decomposed by light irradiation and that the discoloration thereof and the deterioration of the ultraviolet light-absorbency thereof are caused as a function of time. Accordingly, there has been a weak point in the chemical stability of the esters for use thereof in combination with the cosmetics, etc. for a long time period. And, although considerations such as coloring the product preliminarily have been paid concerning the discoloration of the esters of p-dimethylaminobenzoic acid, any method for fundamentally settling the deterioration of ultraviolet light absorbency accompanying the decomposition of the esters has not been known.

Although a great number of UVB absorbing compounds have been known to show the same behavior as that of the esters of p-dimethylaminobenzoic acid represented by the formula (I), it has been surprisingly found by the present inventors that, of the above-mentioned UVB absorbing compounds, the esters of p-dimethylaminobenzoic acid of the formula (I), and the esters of p-methoxycinnamic acid of the formula (II):

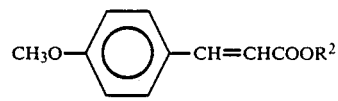

(II) are specifically stabilized by the novel benzylidene compounds of the formula (IV):

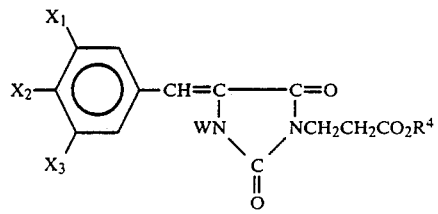

On the basis of the above-mentioned finding, the present inventors have completed the present invention.

The present invention is more effective in sunburn-preventing cosmetics, in preventing yellowing of fibers, resins, etc. and in protecting containers, packing materials and the contents therein from ultraviolet lights, and the present invention can be applied in broad fields such as paints, resins, medicines, foodstuffs and cosmetics. Since the above-mentioned novel compounds of the formula (IV) have the UVA absorbency, in the case where the compound of the formula (IV) is used in combination with the above-mentioned UVB absorbing compounds according to the present invention, not only these UVB absorbing compounds are stabilized but also UVA is absorbed, and accordingly, the present invention is particularly applied advantageously in sunburn-preventing cosmetics.

SUMMARY OF THE INVENTION

In a first aspect of the present invention, there is provided a process for stabilizing a UVB absorbing compound which comprises adding to said UVB absorbing compound at least one UVA absorbing compound in an amount of 0.1–10 parts by weight based on 1 part by weight of UVB absorbing compound, the said UVB absorbing compound being selected from the group consisting of p-dimethylaminobenzoic acid esters of the formula (I):

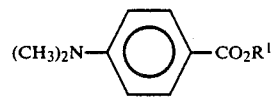

wherein $R^1$ is a $C_1$–$C_8$ linear alkyl group or a $C_3$–$C_8$ branched alkyl group and p-methoxycinnamic acid esters of the formula (II):

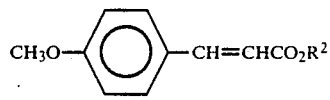

wherein $R^2$ is a $C^1$–$C^8$ linear alkyl group or a $C_3$–$C_8$ branched or cyclic alkyl group, and said at least one UVA absorbing compound being selected from the group consisting of benzylidene compounds of the formula (IV):

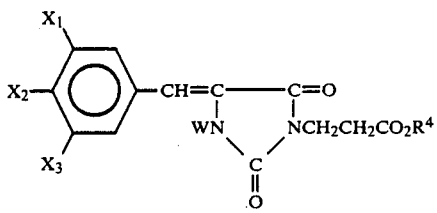

wherein $X^1$ and $X^3$ are independently a hydrogen atom or a methoxyl group, $X_2$ is a hydroxyl group or a methoxyl group, W is a hydrogen atom or a $-CH_2CH_2CO_2R^4$ group, and $R^4$ is a $C_1-C_{18}$ linear alkyl group or a $C_3-C_8$ branched or substituted or non-substituted cyclohexyl group.

In a second aspect of the present invention, there is provided a UV absorber comprising at least one UVB absorbing compound and at least one UVA absorbing compound in a weight ratio of 1:0.1–1:10, said at least one UVB absorbing compound being selected from the group consisting of p-dimethylaminobenzoic acid esters of the formula (I):

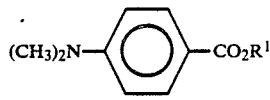

wherein $R^1$ is a $C_1-C_8$ linear alkyl group or a $C_3-C_8$ branched alkyl group and p-methoxycinnamic acid esters of the formula (II):

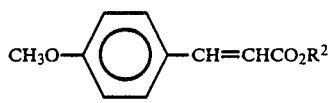

wherein $R^2$ is a $C_1-C_8$ linear alkyl group or a $C_3-C_8$ branched or cyclic alkyl group, and said at least one UVA absorbing compound being selected from the group consisting of benzylidene compounds of the formula (IV):

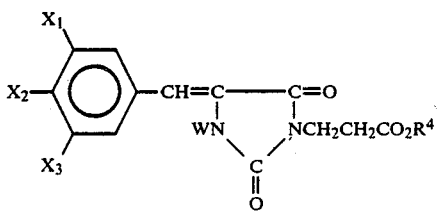

wherein $X_1$ and $X_3$ are independently a hydrogen atom or a methoxyl group, $X_2$ is a hydroxyl group or a methoxyl group, W is a hydrogen atom or a $-CH_2CH_2CO_2R^4$ group and $R^4$ is a $C_1-C_{18}$ linear alkyl group or a $C_3-C_{18}$ branched or substituted or non-substituted cyclohexyl group.

And, in a third aspect of the present invention, there is provided a cosmetic composition containing at least one UVB absorbing compound and at least one UVA absorbing compound in a weight ratio of 1:0.1–1:10, said at least one UVB absorbing compound being selected from the group consisting of p-dimethylaminobenzoic acid esters of the formula (I):

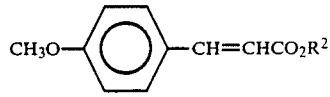

wherein $R^1$ is a $C_1-C_8$ linear alkyl group or a $C_3-C_8$ branched alkyl group and p-methoxycinnamic acid esters of the formula (II):

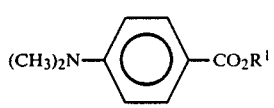

wherein $R^2$ is a $C_1-C_8$ linear alkyl group or a $C_3-C_8$ branched or cyclic alkyl group, and said at least one UVA absorbing compound being selected from the group consisting of benzylidene compounds of the formula (IV):

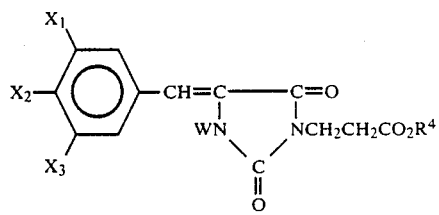

wherein $X_1$ and $X_3$ are independently a hydrogen atom or a methoxyl group, $X_2$ is a hydroxyl group or a methoxyl group, W is a hydrogen atom or a $-CH_2CH_2CO_2R^4$ group, and $R^4$ is a $C_1-C_{18}$ linear alkyl group or a $C_3-C_{18}$ branched or substituted or non-substituted cyclohexyl group.

BRIEF DESCRIPTION OF THE FIGURES

Of the attached drawing, FIG. 7 shows the results of Example 6. Namely, the time (hour) is shown in the abscissa of FIG. 7 and the remaining rate of 2-ethylhexyl p-dimethylaminobenzoate is shown in the ordinate of FIG. 7. Furthermore, the numerals on the right side of FIG. 7 show the amount of addition of 2-ethylhexyl 4-(3,4-dimethoxyphenyl methylene-2,5-dioxo-1-imidazolidinepropionate (mol % thereof to 2-ethylhexyl p-dimethylaminobenzoate).

DETAILED DESCRIPTION OF THE INVENTION

Figure 1:
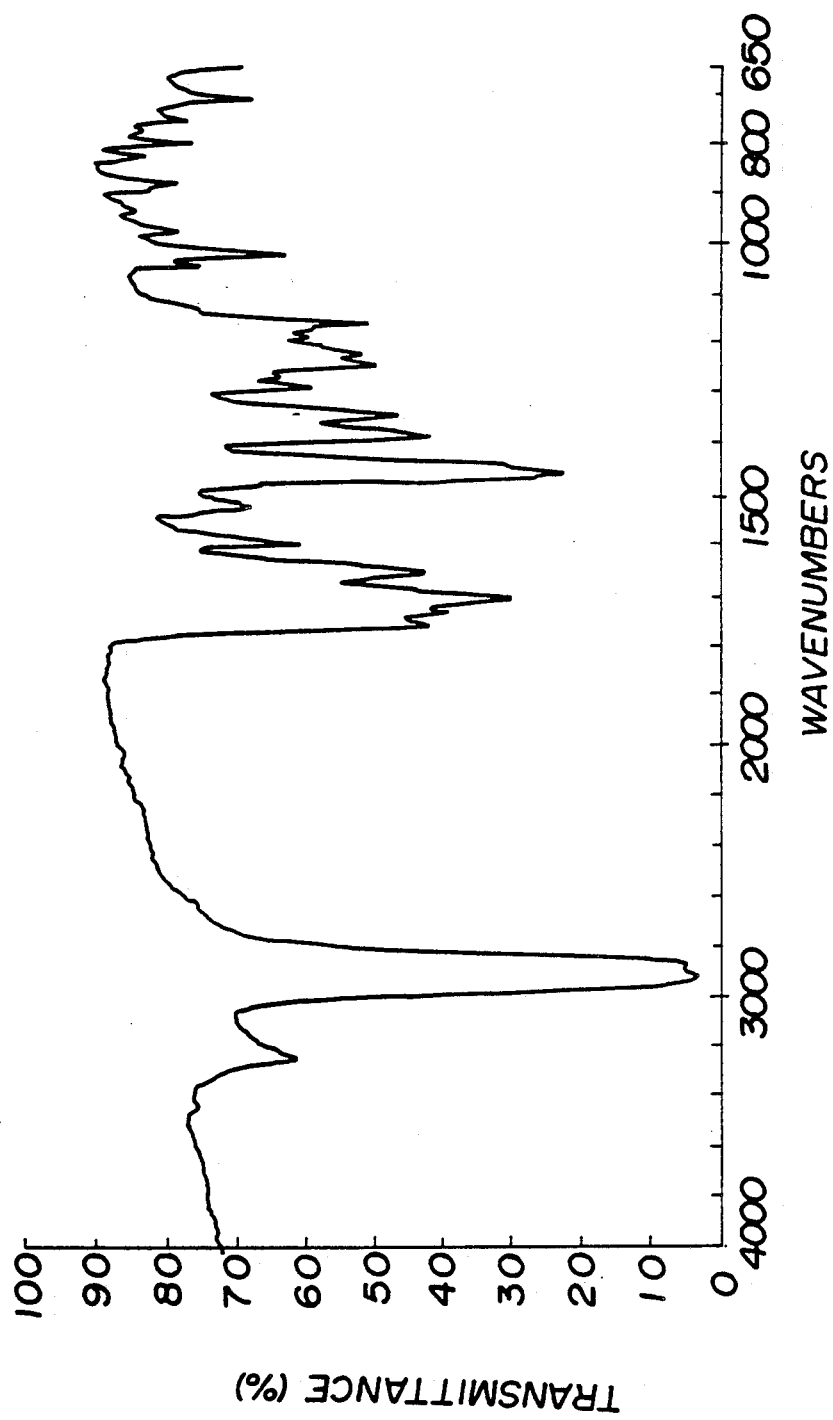
FIGS. 1 to 6 are respectively the IR charts of the six typical examples of the compounds of the formula (IV) (Refer to Example 1)
Figure 2:
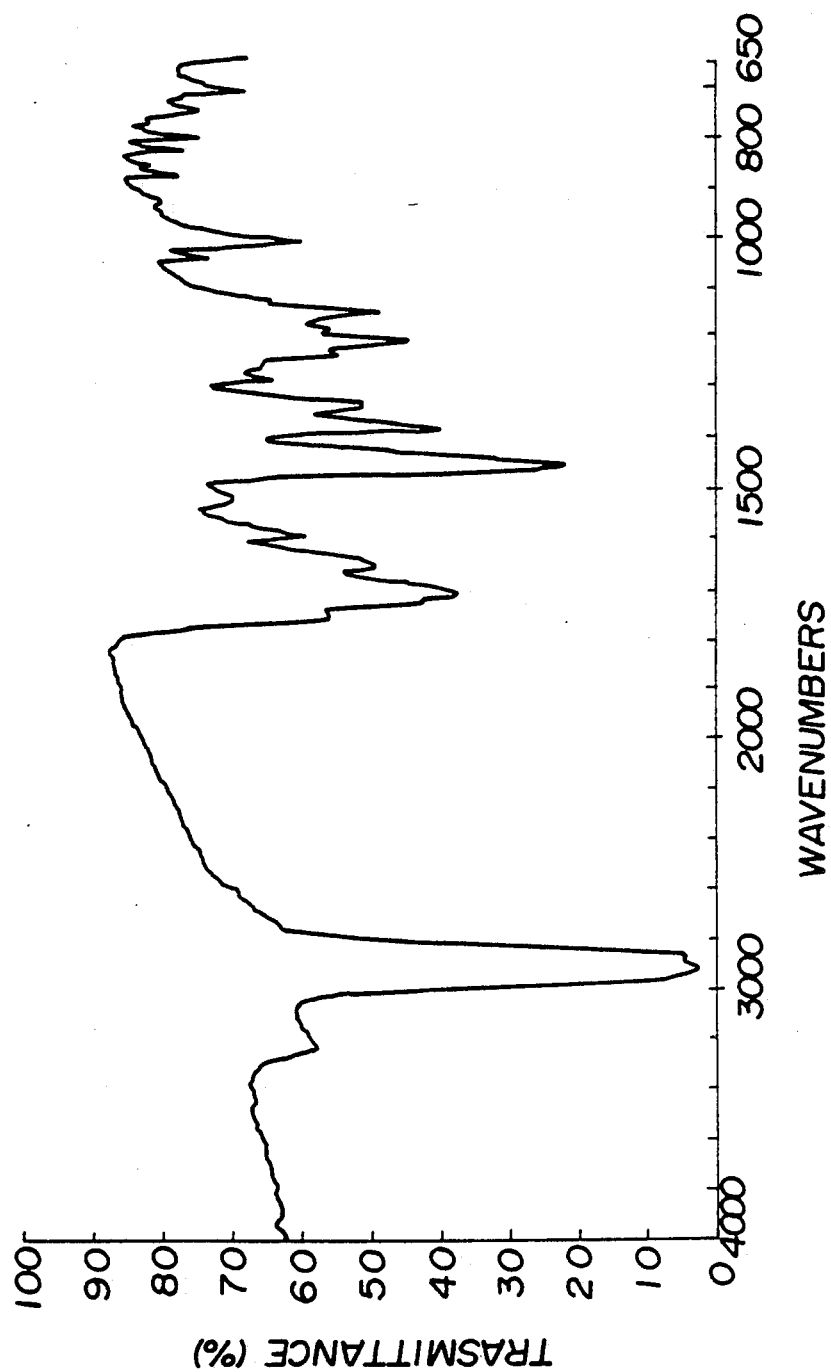
Figure 3:
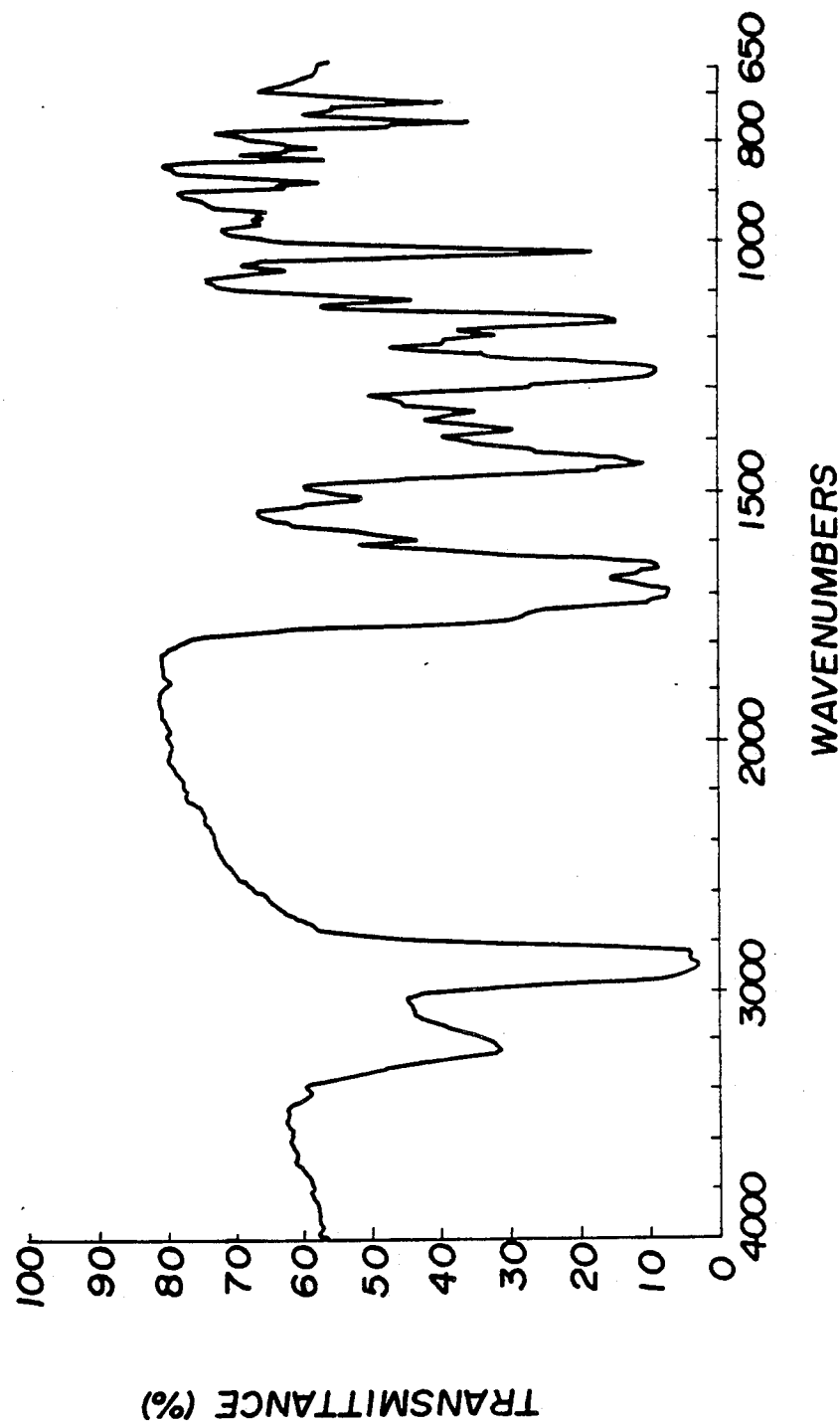
Figure 4:
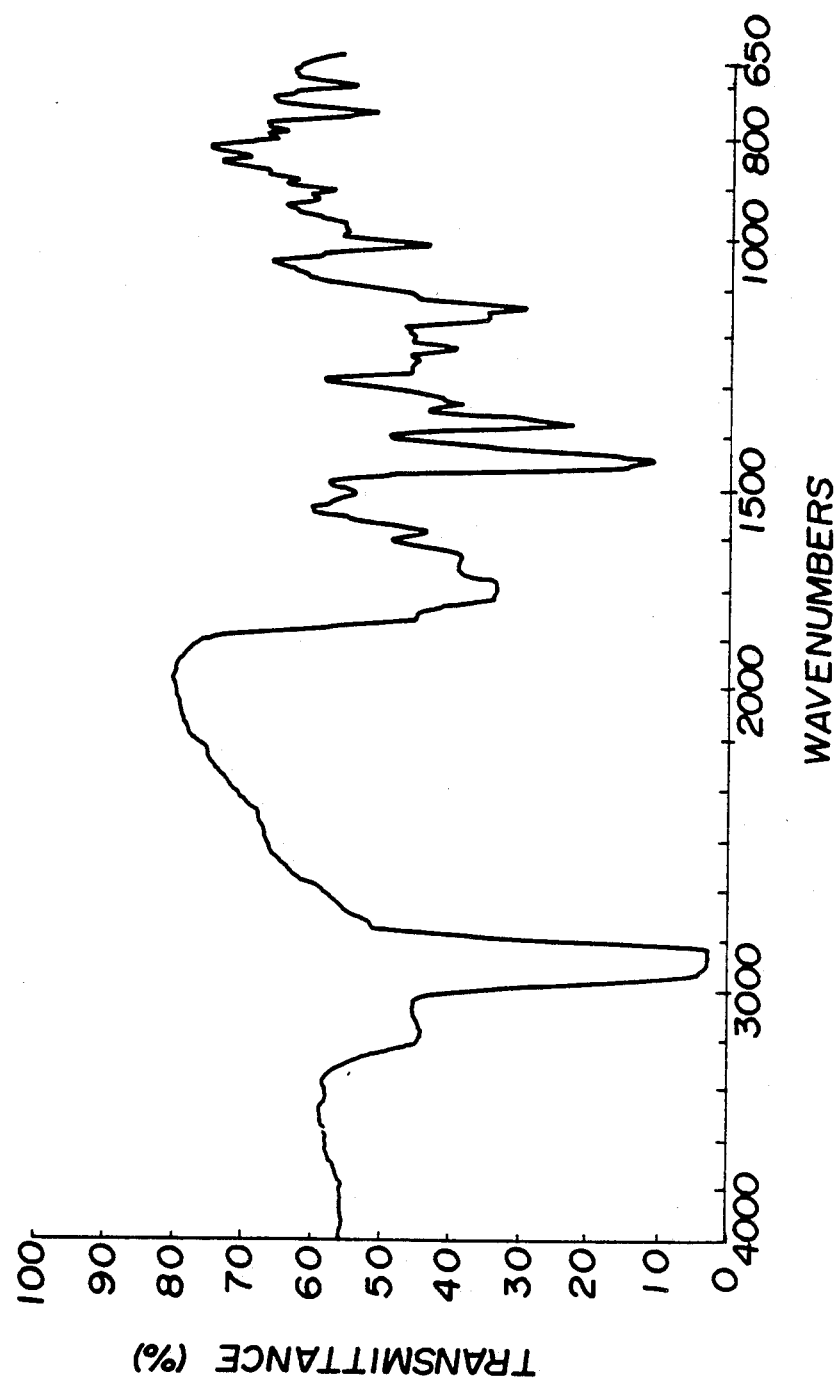
Figure 5:
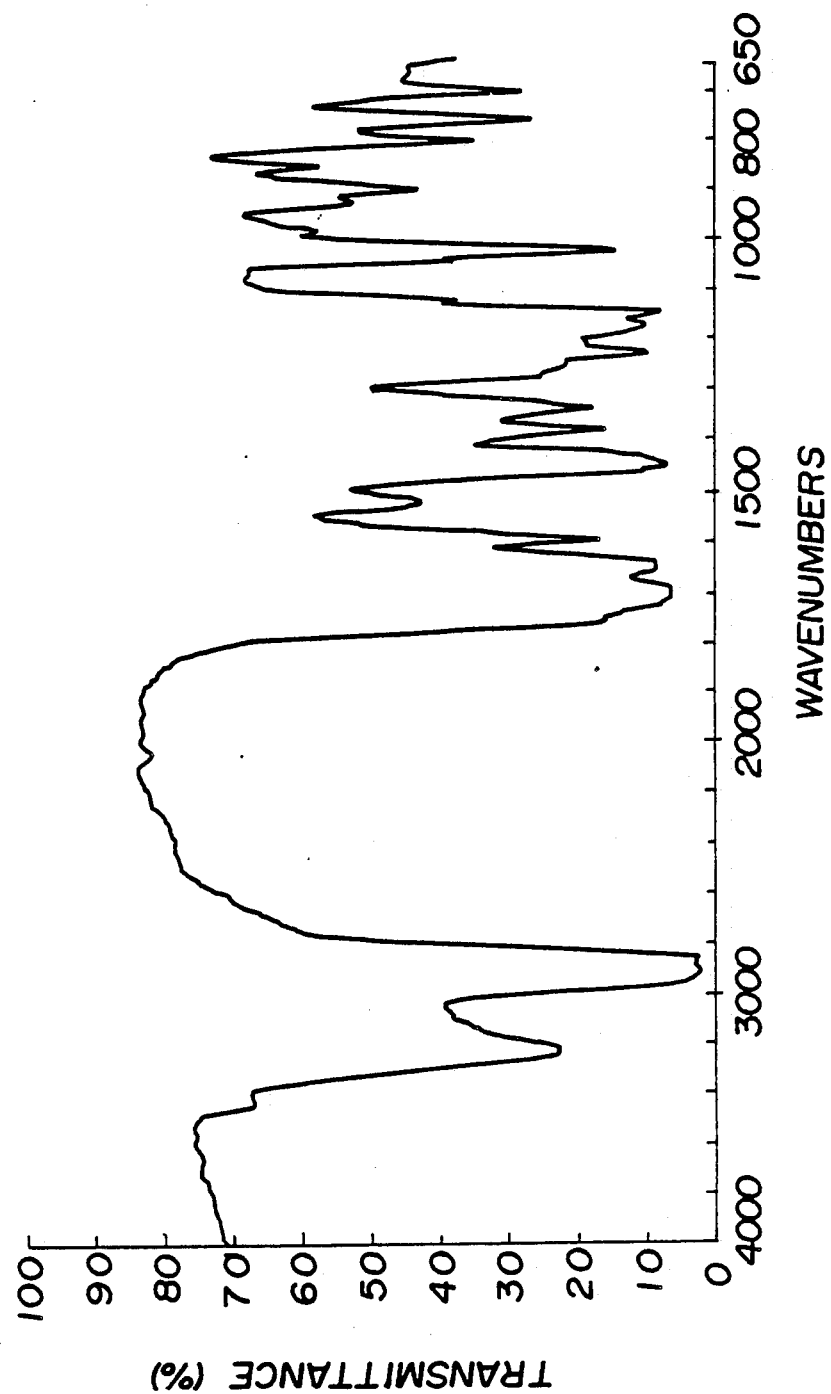
Figure 6:
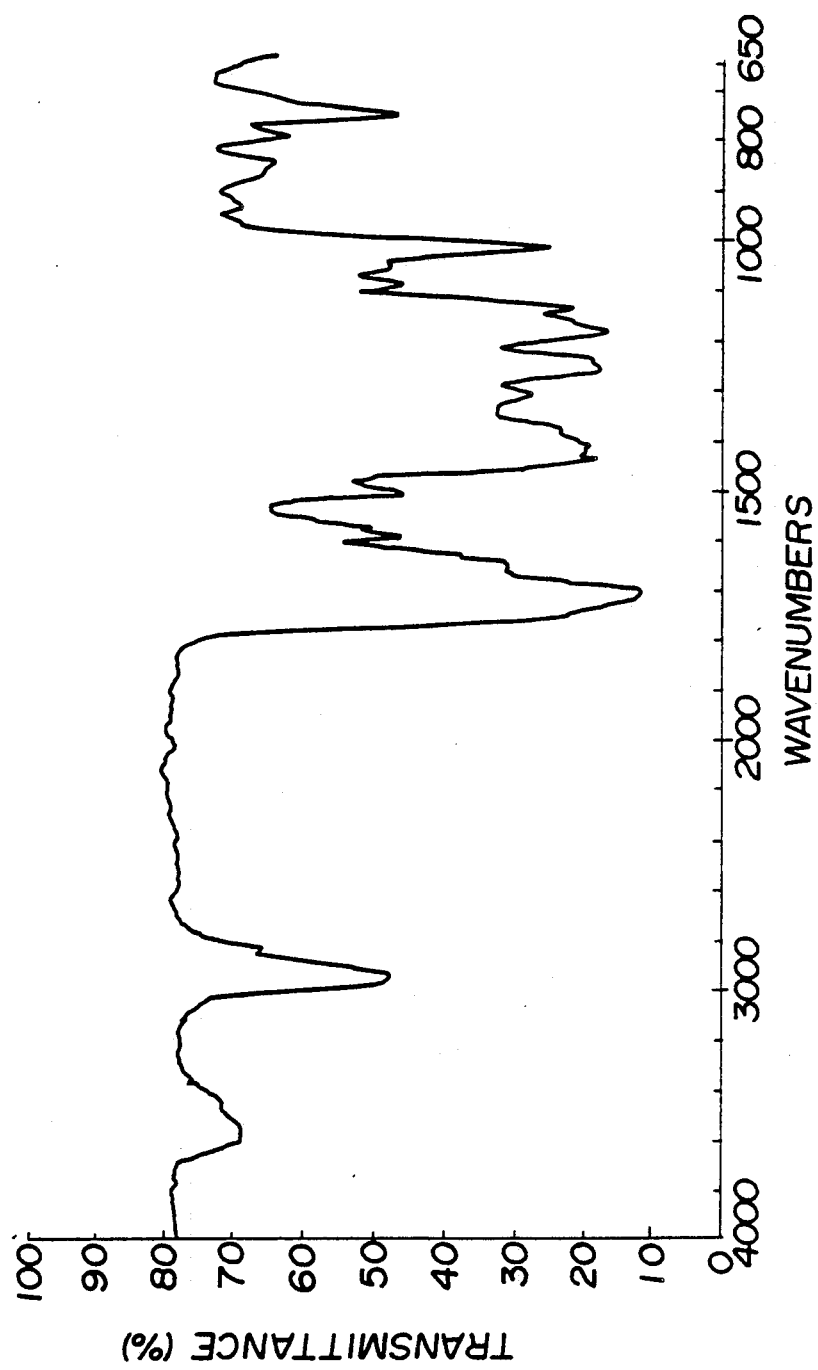

The present invention relates to the method for preventing the deterioration of the quality of the above-mentioned, specified UVB absorbing compounds by combining one or more than two of the above-mentioned, specified UVA absorbing compounds therewith.

A first class of compounds to be stabilized according to the present invention are p-dimethylaminobenzoic acid esters of the formula (I):

wherein $R^1$ is a $C_1-C_8$ linear alkyl group or a $C_3-C_8$ branched alkyl group, preferably, those compounds of the formula (I) wherein $R^1$ is an ethyl, n-butyl, i-butyl, n-amyl, i-amyl, n-octyl or 2-ethylhexyl group, and most preferably 2-ethylhexyl p-dimethylaminobenzoate which is commercially available as "Escalol 507".

A second class of compounds are p-methoxycinnamic acid esters of the formula (II):

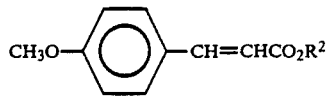

wherein $R^2$ is a $C_1-C_8$ linear alkyl group or a $C_3-C_8$ branched or cyclic alkyl group, preferably those compound of the formula (II) wherein $R^2$ is an n-propyl, i-propyl, i-amyl, 2-ethylhexyl or cyclohexyl group, and most preferably 2-ethylhexyl p-methoxycinnamate which is commercially available as "Parsol MCX".

2-hydroxy-4-methoxybenzophenone of the formula:

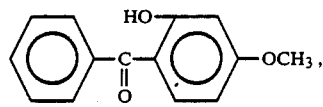

a UVB absorbing compound and commercially available as "Oxybenzone", is mentioned herein as a control compound.

UVA absorbing compounds which are incorporated for the specified UVB absorbing compounds to be stabilized from sun light exposure according to the present invention are novel benzylidene compounds of the formula (IV):

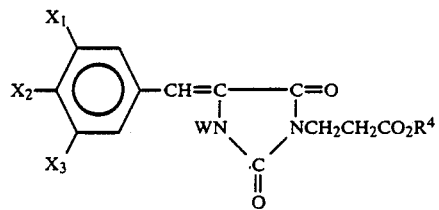

wherein $X_1$ and $X_3$ are independently a hydrogen atom or a methoxyl group, $X_2$ is a hydroxyl group or a methoxyl group, W is a hydrogen atom or a $-CH_2CH_2R^4$ group, and $R^4$ is a $C_1-C$ linear alkyl group or a $C_3-C_{18}$ branched or substituted or non-substituted cyclohexyl group, preferably those compounds of the formula (IV) wherein $X_1$ and $X_2$ are each a methoxyl group, $X_3$ is a hydrogen atom, W is a hydrogen atom or a $-CH_2CH_2CO_2R^4$ group, and $R^4$ is a methyl, ethyl, i-propyl, n-butyl, i-butyl, n-amyl, i-amyl, n-hexyl, cyclohexyl, n-octyl, 2-ethylhexyl, 2,2,4-trimethylcyclohexyl, decyl, lauryl, myristyl, cetyl or stearyl group, more preferably those compounds of the formula (IV) wherein $X_1$ and $X_2$ are each a methoxyl group, $X_3$ is a hydrogen atom, W is a hydrogen atom or a $-CH_2CH_2CO_2R^4$ group, and $R^4$ is a methyl, ethyl, n-butyl, i-butyl, or 2-ethylhexyl group, and most preferably 2-ethylhexyl 4-(3,4-dimethoxyphenyl)methylene-2,5-dioxo-1-imidazolidinepropionate.

The benzylidene compounds can be prepared by a process which comprises:

an aromatic aldehyde of the formula (V) and a hydantoin of the formula (VI) are condensed in the presence of a basic catalyst, and an acrylic ester of the formula (VIII) is subjected to Michael addition to the produced benzalhydantoin of the formula (VII).

THe reaction scheme in this preparation process is as shown below:

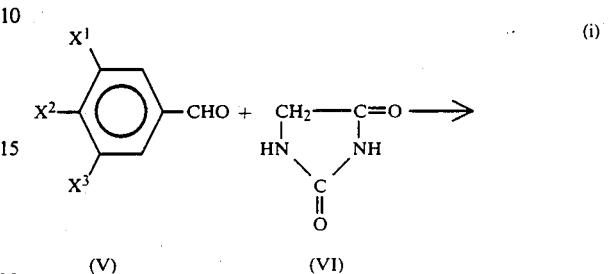

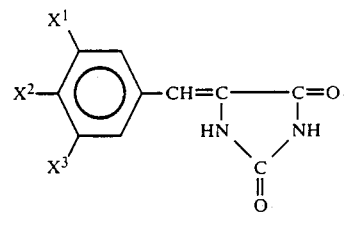

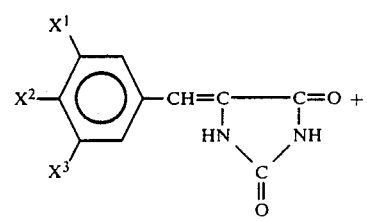

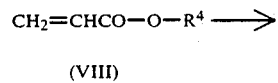

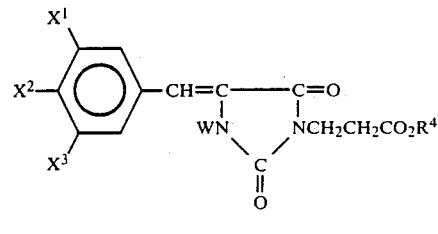

wherein $X^1, X^2, X^3$, W and $R^4$ are as defined above

The condensation reaction of an aromatic aldehyde of the formula (V) and a hydantoin of the formula (VI) is carried out at a temperature of 0 to 150° C.

As the basic catalyst, there can be used an amine such as piperidine, triethyl amine, amino acid, aqueout ammonia, a metal alcoholate such as sodium alcoholate or potassium alcoholate, sodium acetate, sodium hydroxide, potassium hydroxide, and the like.

The reaction for Michael addition of an acrylic ester of the formula (VIII) to the benzalhydantoin of the formula (VII) is carried out at a temperature of 20 to 200° C.

Examples of the benzylidene compounds according to this invention are:

dimethyl 4-(3,4-dimethoxyphenyl methylene)-2,5-dioxo-1 3-imidazolidinedipropionate, diethyl 4-(3,4-dimethoxyphenylmethylene)-2,5-dioxo-1,3-imidazolidinedipropionate, diisopropyl 4-(3,4-dimethoxyphenyl methylene)-2,5-dioxo-1,3-imidazolidinedipropionate, di-n-butyl 4-(3,4-dimethoxyphenyl methylene-2,5-dioxo-1,3-imidazolidinedipropionate, diisobutyl 4-(3,4-dimethoxyphenyl methylene-2,5-dioxo-1,3-imidazolidinepropionate, bis(2-ethylhexyl)4-(3,4-dimethoxyphenyl methylene)-2, 5-dioxo-1,3-imidazolidinedipropionate, isopropyl 4-(3,4-dimethoxyphenyl -methylene)-2,5-dioxo-1-imidazolidinepropionate, methyl 4-(3,4-dimethoxyphenyl methylene)2,5-dioxo-1-imidazolidinepropionate, ethyl 4-(3,4-dimethoxyphenyl methylene)-2,5-dioxo-1-imidazolidinepropionate, n-butyl 4-(3,4-dimethoxyphenylmethylene)-2,5-dioxo-1-imidazolidinepropionate, isobutyl 4-(3,4-dimethoxyphenyl methylene)-2,5-dioxo-1-imidazolidinepropionate, 2-ethylhexyl 4-(3,4-dimethoxyphenyl methylene)-2,5-dioxo-1-imidazolidinepropionate, ethyl 4-(4-methoxyphenyl methylene)-2,5-dioxo-1-imidazolidinepropionate, and ethyl 4-(3,4,5-trimethoxyphenyl methylene)-2,5-dioxo-1-imidazolidinepropionate.

The compounds represented by the general formula (IV) have high absorptivity of ultraviolet rays of long wavelength region (320–400 nm) and are, owing to the effect of $R^4$, soluble in various kinds of animal and vegetable oils, fats and oils, and other organic solvents, as compared with the known compounds, for example, N-benzoyl-α-dehydrotyrosine and O-methyl-N-benzoyl-α-dehydrotyrosine. Incidentally, ultraviolet rays of wavelength 320–400 nm are believed to cause change in vascular wall and elastic fiber in the skin and damage to the skin sensitive or usually exposed to sun light, and to enhance the action of UVB. See J. Willis et al., The Journal of Investigative Dermatology, 59(6), P.416 (1973). Ultraviolet rays of wavelength 290–320 nm are believed to cause erythema of the skin, and ultraviolet rays of wavelength 300–320 nm are considered to cause deterioration of the resins such as polyethylene, polypropylene, polyvinyl chloride, etc.

Thus, the UVA absorbing compounds of the general formula (IV) can be well dissolved in various kinds of animal and vegetable oils, fats and oil, and other organic solvents, and can provide stable compositions when they are added in the cosmetic preparations such as cream, milky lotion, foundation, hair cream, anti-sunburn oil, etc., in combination with the inventive UVB absorbing compounds. Also, when these compounds are added in combination with the UVB absorbing compounds to the resins such as polyethylene, polypropylene, polystyrene, polyvinyl chloride, ABS resin, polycarbonate, the UVB and UVA absorbing compounds have good compatibility with these resins.

The compounds represented by the formula (IV) have high UV absorptivity and excellent light and heat stability and are also non-stimulant and non-injurious to the skin, hair, mucosae and other tissues of the human body, so that when these compounds are blended in combination with the inventive UVB absorbing compound(s) in a suitable amount (selected from within the range of 0.1 to 20% by weight according to the purpose of use) in various kinds of cosmetic preparations such as oil, lotion, cream, milky lotion, hair rinse, hair conditioner, liquid foundation, lipstick, foundation, face powder, aerosol, these cosmetic preparations prove to be ones which have excellent ultraviolet absorptivity and are stable to light and heat.

The stabilization of a UVB absorbing compound according to the present invention by a UVA absorbing compound according to the present invention is carried out by adding to said UVB absorbing compound at least one UVA absorbing compound in an amount of 0.1 to 10 parts by weight, preferably 0.5 to 5 parts by weight per one part by weight of said UVB absorbing compound.

The amount of addition of said UVA absorbing compound necessary for stabilizing said UVB absorbing compound depends upon the object, the use and the combining composition of the product, however, as has been shown above, it is generally desirable to combine 0.1 to 10 parts by weight, preferably 0.5 to 5 parts by weight of said UVA absorbing compound per one part by weight of said UVB absorbing compound.

Furthermore, in order to stabilize said UVB absorbing compounds, although it is necessary that said UVA absorbing compounds have been dissolved in the system, in the case where said UVB absorbing compound dissolves said UVA absorbing compound, the latter may be dissolved in the former or another solvent may be used for that purpose.

The products with which a UVB absorbing compound according to the present invention and a UVA absorbing compound according to the present invention can be combined are the sunburn-preventing cosmetics and the yellowing-preventing agents of fibers and resins, etc., and as the form of the products, liquid form products of solubilizable series, emulsified series, water-/oil two layer series, powdery dispersed series etc., and other form products such as mixing to powders, mixing and kneading to solids and painting to solids may be mentioned.

In the case of the products of liquid form, as the basic agent, any one of water, organic solvents, animal oils and vegetable oils may be used, and in the case where a UVB absorbing compounds according to the present invention is a liquid, the liquid itself may be used as the basic agent. In the case of kneading with a resin, as the basic agent, any one of polyvinyl chloride, polyethylene, polypropylene, polystyrene, ABS resin, polycarbonate, etc., may be used.

The UVB absorbing compounds according to the present invention may be used in combination of more than two kinds thereof and may be used in combination of another ultraviolet light absorbing agent such as the ultraviolet light absorbing agents of benzophenone series, the ultraviolet light absorbing agents of triazole series, the ultraviolet light absorbing agents of dibenzoylmethane series.

Furthermore, within the quantitative and qualitative range of not spoiling the effect of the present invention, organic and inorganic additives may be added for the purpose of coloring and viscosity-increasing as the occasion demands.

The UV absorber according to the present invention comprises at least one UVB absorbing compound according to the present invention and at least one UVA absorbing compound according to the present invention in the weight ratio of 1:0.1 to 1:10, preferably 1:0.5 to 1:5, and can be used instead of known UV absorbers, in particular known UVB absorbers.

The cosmetic composition according to the present invention contains at least one UVB absorbing compound according to the present invention and at least one UVA absorbing compound according to the present invention in the weight ratio of 1:0.1 to 1:10, preferably 1:0.5 to 1:5.

The cosmetic compositions according to the present invention are composed of at least one UVB absorbing compound according to the present invention and at least one UVA absorbing compound according to the present invention and the known components generally used in cosmetic compositions, that is, an oil phase component, an aqueous phase component, a powder component and/or a surfactant component for emulsifying, dispersing or solubilizing these component materials.

Examples of the known components usable in the composition of the present invention are shown below:

As an oil phase component, animal and vegetable oils such as beeswax, Japan wax, whale wax, carnauba wax, candelilla wax, cacao oil, cetyl alcohol, stearyl alcohol, oleic acid, stearic acid, lanoline, olive oil, tsubaki oil, avocado oil, coconut oil, jojoba oil, cottonseed oil, castor oil, oleyl alcohol, squalane ; mineral oils and fats such as solid paraffin, ceresine, microcrystalline wax, vaseline, liquid paraffin, silicone oil ; and synthetic oils and fats such as isopropyl myristate, isopropyl palmitate, oleyl oleate, isostearic acid, octyl dodecanol, synthetic polyether may be exemplified.

As an aqueous phase component, polyhydric alcohols such as glycerol, ethylene glycol, propylene glycol, diethylene glycol, dipropylene glycol, triethylene glycol, diglycerol, polyglycerol, EO addition product of glycerol, PO addition product of glycerol, 1,3-butylene glycol and, 1,4-butylene glycol; water-soluble high polymers such as polyethylene glycol, polypropylene glycol, Quine Seed gum, Tragacanth gum, alginates, pectin, carboxymethylcellulose, hyaluronic acid, water-soluble chitin, polyvinyl alcohol, cationized cellulose, condensate of aliphatic acid polypeptide; sugar-alcohols such as sorbitol, xylitol, mannitol, and EO and PO addition products thereof; organic acids such as ascorbic acid, citric acid, gluconic acid, succinic acid, acetic acid, oxalic acid, tartaric acid, lactic acid, EDTA, pyrrolidonecarboxylic acid, various amino acids and the salts thereof; and others such as ethanol, isopropanol, urea, phosphoric acid and the salts thereof may be exemplified.

As a surfactant, nonionic surface active agents such as polyoxyethylene fatty acid partial ester, polyoxyethylene sorbitan fatty acid partial ester, polyoxyethylene glycerol fatty acid partial ester, polyglycerol fatty acid partial ester, fatty acid alkanol amide, fatty acid alkanol amide-ethylene oxide addition product, polyoxyethylene glycerol fatty acid, monoglycerol pyroglutamate, glycerol acylglutamate; anionic surface active agents such as alkyl sulfate, polyoxyethylene alkyl sulfate, fatty acid amide ether sulfate, alkylbenzene sulfonate, alkyloxy sulfonate, sulfosuccinic acid higher alcohol ester salts, N-long-chain fatty acid acyl-N-methyl-taurine salts, fatty acid salts, N-long-chain acyl glutamate, N-long-chain acyl sarcosine salts, monoalkyl phosphate; amphoteric surface active agents such as carboxybetaine type, imidazoline type, lecithin, aminosulfcnic acid type, alkylamine oxide type, Nα, Nα-dimethyl or Nα, Nα, Nα-trimethyl-Nε-acyl basic amino acids; and cationic surface active agents such as dialkyldimethylammonium chloride, alkyltrimethylammonium chloride, fatty acid acylalginine ethyl ester salts, may be exemplified.

As a powder, inorganic powders such as talc, kaolin, titanium oxide, titanium-coated mica, mica, iron oxide, silicic ultramarine, prussian blue, zinc white, clay, precipitated calcium carbonate, bismuth oxychloride, bentonite, montmorillonite; and organic powders such as N-long-chain acyl basic amino acids, guanine, pearl laminated resin, may be exemplified.

The cosmetic compositions of the present invention may further contain usually used cosmetic adjuvants such as extracts of placenta, vitamin C, vitamin E and derivatives thereof, skin depigmental agent such as arbutin and the other glycosides of hydroquinone, thickening agent, softener, wetting agent, super-fatting agent, relaxing agent, moistening agent, preservative, defoaming agent, chelating agent, protective colloidal agent, perfume, dye for coloring the composition itself or the skin, and any other materials normally used in the cosmetics.

The cosmetic compositions of the present invention can be made into desired forms such as solution, emulsion, kneaded mixture, solid (pressed preparation), powder, etc., by properly selecting and adjusting the type and amount of the components compounded. As uses of the cosmetic compositions of the present invention, sun oil, lotion, cream, milky lotion, hair rinse, hair conditioner, liquid foundation, lipstick, foundation, face powder, aerosol, may be exemplified.

The contents of the UVB absorbing and UVA absorbing compounds of the present invention in the cosmetic compositions of the present invention may vary depending on the composition of the compounding ingredients and the sun protecting factors (SPF), but the contents of the UVB absorbing compounds and the UVA absorbing compounds are usually 0.1–15.0% by weight and 0.01–15.0% by weight, respectively, of the composition.

As the ultraviolet absorber to be contained in the cosmetic compositions of the present invention, at least one of the inventive UVB absorbing compounds is used in combination with at least one of the inventive UVA absorbing compounds. Other types of ultraviolet absorber may be also used in combination with the inventive UVB and UVA absorbing compounds.

As such other types of ultraviolet absorbers that can be used in the cosmetic compositions of the present invention, camphor derivatives such as p-methylbenzylidene-D,L-camphor or sodium sulfonate thereof; benzophenones such as sodium 2-phenylbenzimidazole-5-sulfonate, sodium 3,4-dimethylphenylglyoxylate, isooctyl 4-phenylbenzophenone-2-carboxylate; and 2-phenyl-5-methylbenzoxazole, and the like may be exemplified.

They can be used with an inorganic powder such as titanium oxide which serves as a scattering agent.

The present invention can exhibit the following effects:

Namely, the present invention can prevent the time-dependent discoloration of the UVB absorbing compounds according to the present invention and also can prevent the deterioration of the ultraviolet light-absorbency thereof. Further, the benzylidene compounds represented by the formula (IV) have a large absorption band in the long wave ultraviolet light region of 320 to 400 nm. On the other hand, for instance, since the ester of p-dimethylaminobenzoic acid represented by the formula (I) absorb the ultraviolet light of the medium wave length region of 290 to 320 nm, using the above-mentioned two kinds of compounds in combination can afford effective protection from both the medium and the long wave length ultraviolet lights.

As has been described above, the utilization range of the present invention covers the cosmetic industry, the plastic industry, the organic chemical industry, the photographic industry, the foodstuff industry, the textile industry, etc. and is extremely wide.

EXAMPLE

Typical examples of the compound of the general formula (IV), and the maximum absorptivity wavelength (the UV wavelength at which the compounds show the maximum UV absorptivity) and other properties measured with the typical examples are shown in Tables 1 and 2 as Example 1.

TABLE 1

Example 1

$$\begin{array}{c} X_1 \\ X_2 \\ X_3 \end{array} \!\!-\!\!\bigcirc\!\!-\!\!CH\!=\!C\!\!-\!\!C\!=\!O \\ \quad\quad |\quad\quad\quad | \\ \quad WN\quad NCH_2CH_2CO_2R^4 \\ \quad\quad\quad\backslash\ /\!\! \\ \quad\quad\quad C \\ \quad\quad\quad \| \\ \quad\quad\quad O$$
(IV)

| No. | Compound | $X^1$ | $X^2$ | $X^3$ | W | $R^4$ |
|---|---|---|---|---|---|---|
| 1 | Methyl 4-(3,4-dimethoxyphenylmethylene)-2,5-dioxo-1-imidazolidinepropionate | $OCH_3$ | $OCH_3$ | H | H | $CH_3$ |
| 2 | Ethyl 4-(3,4-dimethoxyphenylmethylene)-2,5-dioxo-1-imidazolidinepropionate | $OCH_3$ | $OCH_3$ | H | H | $C_2H_5$ |
| 3 | N-butyl 4-(3,4-dimethoxyphenylmethylene)-2,5-dioxo-1-imidazolidinepropionate | $OCH_3$ | $OCH_3$ | H | H | $n\text{-}C_4H_9$ |
| 4 | Iso-butyl 4-(3,4-dimethoxyphenylmethylene)-2,5-dioxo-1-imidazolidinepropionate | $OCH_3$ | $OCH_3$ | H | H | $i\text{-}C_4H_9$ |
| 5 | 2-ethylhexyl 4-(3,4-dimethoxyphenylmethylene)-2,5-dioxo-1-imidazolidinepropionate | $OCH_3$ | $OCH_3$ | H | H | $CH_2CH{\diagdown\atop\diagup}{C_4H_9 \atop C_2H_5}$ |
| 6 | Diethyl 4-(3,4-dimethoxyphenylmethylene)-2,5-dioxo-1,3-imidazolidinedipropionate | $OCH_3$ | $OCH_3$ | H | $CH_2CH_2CO\text{—}O\text{—}R^4$ | $C_2H_5$ |

TABLE 2

Property values of benzylidene compounds represented by the formula (IV)

| No. | Compound | Melting point (°C.) | Max. absorptivity wavelength (nm) | Molecular extinction coefficient | Mass spectrum (m/e) | Elemental analysis (%) Theoretical/Found | C | H | N | IR FIG. NO. |
|---|---|---|---|---|---|---|---|---|---|---|
| 1 | Methyl 4-(3,4-dimethoxyphenylmethylene)-2,5-dioxo-1-imidazolidinepropionate | 183.8–184.8 | 346 | 25300 (4.40) | 334 | Theoretical Found | 57.48 57.52 | 5.43 5.50 | 8.38 8.41 | 1 |
| 2 | Ethyl 4-(3,4-dimethoxyphenylmethylene)-2,5-dioxo-1-imidazolidinepropionate | 161.5–162.6 | 346 | 24900 (4.40) | 348 | Theoretical Found | 58.61 58.35 | 5.79 5.95 | 8.04 7.98 | 2 |
| 3 | N-butyl 4-(3,4-dimethoxyphenylmethylene)-2,5-dioxo-1-imidazolidinepropionate | 132.8–133.6 | 346 | 25200 (4.40) | 376 | Theoretical Found | 60.63 60.58 | 6.43 6.66 | 7.44 7.18 | 3 |
| 4 | Iso-butyl 4-(3,4-dimethoxyphenylmethylene)-2,5-dioxo-1-imidazolinepropionate | 146.5–147.3 | 346 | 24200 (4.38) | 376 | Theoretical Found | 60.63 60.37 | 6.43 6.16 | 7.44 7.22 | 4 |
| 5 | 2-ethylhexyl 4-(3,4-dimethoxyphenylmethylene)-2,5-dioxo-1-imidazolidinepropionate | 102.2–103.2 | 348 | 22800 (4.36) | 432 | Theoretical Found | 63.87 63.90 | 7.46 7.70 | 6.48 6.32 | 5 |
| 6 | Diethyl 4-(3,4-dimethoxyphenylmethylene)-2,5-dioxo-1,3-imidazolidinedipropionate | Oil | 334 | 14100 (4.15) | 448 | Theoretical Found | 58.92 59.02 | 6.29 6.29 | 6.25 6.03 | 6 |

Examples 2–4 illustrate synthesis of some compounds of the general formula (IV).

EXAMPLE 2

Synthesis of n-butyl 4-(3,4-dimethoxyphenylmethylene)-2,5-dioxo-1-imidazolidinepropionate (Compound No. 3)

20 g (80.6 mmol) of 5-(3,4-dimethoxybenzylidine)-hydantoin, 12.4 g (96 mmol) of n-butyl acrylate and 0.90 g (1.6 mmol) of potassium hydroxide were added to 150 ml of dimethylformamide, and the mixture was stirred at 110° C. for 2 hours. The reaction solution was added with 200 ml of water and extracted with 500 ml of ethyl acetate. The extract was dried with sodium sulfate and then the solvent was distilled off under reduced pressure Toluene was added to the residue and the precipitated crystals were dried to obtain 24.7 g of n-butyl 4-(3,4-dimethoxyphenylmethylene)-2,5-dioxo-1-imidazolidinepropionate (yield: 81.5%).

EXAMPLE 3

Synthesis of 2-ethylhexyl 4-(3,4-dimethoxyphenylmethylene)-2,5-dioxo-1-imidazolidinepropionate (Compound No. 5)

20 g (80.6 mmol) of 5-(3,4-dimethoxybenzylidene)-hydantoin, 17.8 g (96 mmol) of 2-ethylhexyl acrylate and 0.90 g (1.6 mmol) of potassium hydroxide were added to 150 ml of dimethylformamide, and the mixture was stirred at 110° C. for 2 hours. After cooling, the reaction solution was added with 200 ml of water and extracted with 500 ml of ethyl acetate. The extract was dried with sodium sulfate and then the solvent was distilled off under reduced pressure. The residue was recrystallized with toluene-n-hexane (1:1) and the precipitated crystals were dried to obtain 27.1 g of 2-ethylhexyl 4-(3,4-dimethoxyphenylmethylene)-2,5-dioxo-1-imidazolidinepropionate (yield: 77.8%).

EXAMPLE 4

Synthesis of diethyl 4-(3,4-dimethoxyphenylmethylene)-2, 5-dioxo-1,3-imidazolidinedipropionate (Compound No. 6)

20 g (80.6 mmol) of 5-(3,4-dimethoxybenzylidene)-hydantoin, 17.7 g (177 mmol) of ethyl acrylate and 0.90 g (1.6 mmol) of potassium hydroxide were added to 150 ml of dimethylformamide (DMF), and the mixture was stirred at 110° C. for 2 hours After cooling, the reaction solution was added with 200 ml of water and extracted with 500 ml of ethyl acetate. The extract was dried with sodium sulfate and the solvent was distilled off under reduced pressure. The residue was separated and purified by silica gel column chromatography [eluent: toluene/ethyl acetate (3/1)] to obtain 22.5 g of diethyl 4-(3,4-dimethoxyphenylmethylene)-2, 5-dioxo-1,3-imidazolidinedipropionate (yield: 62.3%).

The solubility of the compounds in the organic solvents is shown in Table 3 as Example 5.

TABLE 3

Example 5
Solubility* of novel benzylidene compounds of the formula

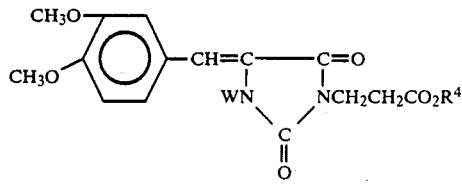

| Compound | | | Solvent | | | |
|---|---|---|---|---|---|---|
| No. | W | $R^4$ | Ethanol | Iso-Propyl myristate | Olive oil | Liquid paraffin |
| 1 | H | $CH_3$ | 1.0 | 1.0 | 1.0 | 1.0 |
| 3 | H | n-Bu | 1.0 | 1.0 | 1.0 | 1.0 |
| 5 | H | 2-Ethylhexyl | 4.0 | 2.0 | 2.0 | 1.0 |
| 6 | $CH_2CH_2CO_2R^4$ | Et | 5.0 | 5.0 | 5.0 | 1.0 |

*Grams of the sample dissolved in 100 ml solvent at 25° C.

Examples 6 to 9 show the effect of stabilization in the case where the benzylidene compounds of the present invention are added to the ester of p-dimethylaminobenzoic acid of the present invention. It is desirable that the UVB absorbing compound remains in an amount of not less than 50% after light irradiation for a few hours.

EXAMPLE 6

Into 100 ml of ethanol, 50 mg of 2-ethylhexyl p-dimethylaminobenzoate and the indicated amounts (in FIG. 7 ) of 2-ethylhexyl 4-(3,4-dimethoxyphenyl methylene)-2,5-dioxo-1-imidazolidinepropionate were dissolved, and the thus formed solution was introduced into a quartz test tube. The test tube was irradiated by an ultraviolet lamp (made by FUNAKOSHI YAKUHIN Co., Ltd., under the name of FUNA UV LIGHT SL-800F) at room temperature, and the remaining rate of 2-ethylhexyl p-dimethylaminobenzoate was measured by the high speed liquid chromatography. The results are shown in FIG. 7.

It was found that the light stability of 2-ethylhexyl p-dimethylaminobenzoate was raised by the addition of 2-ethylhexyl 4-(3,4-dimethoxyphenyl methylene)-2,5-dioxo-1-imidazolidinepropionate.

EXAMPLE 7

Into 100 ml of ethanol, 50 mg o 2-ethylhexyl p-dimethylaminobenzoate were dissolved, and the thus formed solution was introduced into a quartz test tube. Into each of the thus prepared test tubes, 2-ethylhexyl 4-(3,4-dimethoxyphenylmethylene)-2,5-dioxo-1-imidazolidineprdpionate, or 4-(3,4,5-trimethoxyphenyl methylene)2,5-dioxoimidazolidine was added in an amount of one mole per mole of said 2-ethylhexyl p-dimethylaminobenzoate, and the test tubes were irradiated by ultraviolet light from an ultraviolet lamp (made by FUNAKOSHI YAKUHIN Co., Ltd. under the name of FUNA UV LIGHT SL-800F) at room temperature.

The remaining rate of 2-ethylhexyl p-dimethylaminobenzoate in the solution was measured by the high speed liquid chromatography. The results are shown in Table 4.

It was found that the light-stability of the ester of p-dimethylaminobenzoic acid was clearly raised by the addition of the benzylidene derivatives.

TABLE 4

Stabilization of 2-ethylhexyl p-dimethylaminobenzoate by the addition of benzylidene derivatives

| 2-Ethylhexyl p-dimethylaminobenzoate | | Benzylidene derivatives | |
|---|---|---|---|
| Sampling amount (mg) | Remaining rate (%) after 6 hours | Chemical name | Amount of addition (mg) |
| 17.2 | 34.4 | Not added | — |
| 50.0 | 100.0 | 4-(3,4-dimethoxy-phenyl methylene)-2, 5-dioxoimidazolidine | 44.8 |
| 48.5 | 97.0 | 4-(3,4,5-trimethoxy-phenyl)-methylene-2, 5-dioxoimidazolidine | 50.2 |

EXAMPLE 8

Into 100 ml of ethanol, tetrahydrofuran (THF) or 1,4-dioxane, 50 mg of 2-ethylhexyl p-dimethylaminobenzoate and 78 mg of 2-ethylhexyl 4-(3,4-dimethoxyphenyl methylene)-2, 5-dioxo-1-imidazolidinepropionate were dissolved, and the thus formed solution was introduced into a quartz test tube.

The thus prepared test tubes were irradiated, at room temperature, by ultraviolet light from an ultraviolet lamp (made by FUNAKOSHI YAKUHIN Co., Ltd. under the name of FUNA UV LIGHT SL-800F), and the remaining rate of 2-ethylhexyl p-dimethylaminobenzoate in the solution was measured by the high speed liquid chromatography. The results are shown in Table 5.

It was found that the light-stability of 2-ethylhexyl p-dimethylaminobenzoate was raised by the addition of 2-ethylhexyl 4-(3,4-dimethoxyphenyl methylene)-2,5-dioxo-1-imidazolidinepropionate.

TABLE 5

Stabilization of 2-ethylhexyl p-dimethylaminobenzoate in each of the solvents

| Addition amount of 2-ethylhexyl 4-(3,4-dimethoxyphenyl methylene)-2,5-dioxo-1-imidazolidinepropionate (mg) | 2-Ethylhexyl p-dimethylaminobenzoate | | Solvent |
|---|---|---|---|
| | Sampling amount (mg) | Remaining rate after 4 hours (%) | |
| 0.0 | 26.8 | 53.5 | Ethanol |
| 78.0 | 50.0 | 100.0 | Ethanol |
| 0.0 | 25.3 | 50.6 | Dioxane |
| 78.0 | 42.0 | 84.0 | Dioxane |
| 0.0 | 35.7 | 71.4 | THF |
| 78.0 | 50.0 | 100.0 | THF |

EXAMPLE 9

Coloring test was carried out on a cloth to which a ultra-violet light absorbing agent had adhered Namely, a test piece of flannel cloth was immersed in one of the ethanolic solutions No. 1 to 14 of the ultraviolet light absorbing compounds and after exposing the thus immersed piece of cloth to sunlight for 3.5 hours, the degree of coloration of the piece of cloth was measured The degree of coloration was shown by the color difference (ΔE) in the case where the non-treated and non-exposed test piece of cloth was set as the standard The results are shown in Table 6.

TABLE 6

| No. | UVA absorbing compound (concentration) | | UVB absorbing compound (concentration) | | Color difference after 3.5 hours (ΔE) |
|---|---|---|---|---|---|
| 1 | Not added | | Escalol 507 | (0.5%) | 10.13 |
| 2 | DH | (0.5%) | Escalol 507 | (0.5%) | 8.10 |
| 3 | Parsol 1789 | (0.5%) | Escalol 507 | (0.5%) | 11.66 |
| 4 | Not added | | Parsol MCX | (0.5%) | 4.39 |
| 5 | DH | (0.5%) | Parsol MCX | (0.5%) | 2.49 |
| 6 | Parsol 1789 | (0.5%) | Parsol MCX | (0.5%) | 2.91 |
| 7 | Not added | | Homosalate | (0.5%) | 1.75 |
| 8 | DH | (0.5%) | Homosalate | (0.5%) | 2.10 |
| 9 | Parsol 1789 | (0.5%) | Homosalate | (0.5%) | 4.13 |
| 10 | Not added | | Oxybenzone | (0.5%) | 2.93 |
| 11 | DH | (0.5%) | Oxybenzone | (0.5%) | 2.63 |
| 12 | Parsol 1789 | (0.5%) | Oxybenzone | (0.5%) | 4.48 |
| 13 | DH | (0.5%) | Not added | | 0.65 |
| 14 | Parsol 1789 | (0.5%) | Not added | | 5.21 |

Notes:
DH means 2-ethylhexyl 4-(3,4-dimethoxyphenyl-methylene)-2,5-dioxo-1-imidazolidinepropionate, one of the UVA absorbing compounds according to the present invention.
Parsol 1789 means a commercially available UVA absorbing compound of the formula:

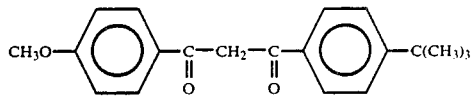

used as a control.
Escalol 507, Parsol MCX, Homosalate (3,3,5-trimethyl-cyclohexyl salicylate) and Oxybenzone are among UVB absorbing compounds, the first two belonging to the UVB absorbing compounds according to the present invention, while the last two being a control.

Typical examples of formulations using the compounds of the present invention are shown as Examples 10 to 22.

EXAMPLE 10: Sun oil

The materials shown below were compounded in the shown amounts to prepare a sun oil. The more advantageous conditions for homogenizing the following composition are to mix the materials while heating at about 40 to 45° C.

| | |
|---|---|
| 2-Ethylhexyl p-dimethylaminobenzoate | 3.0% by weight |
| 2-Ethylhexyl 4-(3,4-dimethoxyphenyl methylene)-2,5-dioxo-1-imidazolidinepropionate | 1.0% by weight |
| Cacao oil | 2.5% by weight |
| Perfume | 0.5% by weight |
| Fatty acid triglyceride ($C_8$–$C_{12}$) | 93% by weight |

EXAMPLE 11: Skin protective cream (O/W type)

Components of (A) and (B) were respectively dissolved under heating according to the following formulations, and they were mixed and cooled to room temperature to prepare a skin protective cream.

| (A) | |
|---|---|
| 2-Ethylhexyl p-methoxy cinnanate | 5.0% by weight |
| Diethyl 4-(3,4-dimethoxyphenyl methylene)-2,5-dioxo-1,3-imidazolidine-dipropionate | 3.0% by weight |
| Fatty acid triglyceride ($C_8$–$C_{12}$) | 8% by weight |
| Cetyl alcohol | 10% by weight |
| Polyoxyethylene cetyl ether (10 E.O.) | 1.5% by weight |
| Polyoxyethylene stearyl ether (10 E.O.) | 6% by weight |
| Polyoxyethylene sorbitan mono-stearate (20 E.O.) | 2% by weight |
| (B) | |
| Glycerin | 1.5% by weight |
| Propylene glycol | 1.5% by weight |
| Sorbitol solution (70%) | 3.5% by weight |
| Sodium pyrrolidonecarboxylate | 0.5% by weight |
| Methyl para-oxybenzoate | 0.2% by weight |
| Water | 57% by weight |

EXAMPLE 12: Skin protective cream (W/O type)

The following components were compounded and treated in the same way as Example 11 to prepare a skin protective cream.

| (A) | |
|---|---|
| 2-Ethylhexylbenzoate | 4.0% by weight |
| Methyl 4-(3,4-dimethoxy phenyl methylene)-2,5-dioxo-2-imidazolidinepropionate | 4.0% by weight |
| Cetyl alcohol | 1.5% by weight |
| Beeswax | 1.5% by weight |
| Paraffin oil | 3% by weight |
| Cholesterol | 1% by weight |
| Fatty acid triglyceride ($C_8$–$C_{12}$) | 8% by weight |
| Glycerin monostearate | 5% by weight |
| Sorbitan monopalmitate | 9% by weight |
| Polyoxyethylene sorbitan mono-stearate (20 E.O.) | 1% by weight |
| Ceresine | 5% by weight |
| Whale wax | 2% by weight |
| Propyl para-oxybenzoate | 0.1% by weight |
| (B) | |
| Glycerin | 1.5% by weight |
| Propylene glycol | 1.5% by weight |
| Sorbitol solution (70%) | 4% by weight |
| Methyl para-oxybenzoate | 0.2% by weight |
| Water | 47.7% by weight |

EXAMPLE 13: Sun milk (milky lotion)

The following components were compounded and treated in the same way as Example 11 to prepare a sun milk.

| (A) | |
|---|---|
| Ethyl p-dimethylamino benzoate | 5% by weight |
| N-butyl 4-(3,4-dimethoxy-phenyl methylene)-2,5-dioxo-1-imidazolidine propionate | 2% by weight |
| Polyoxyethylene cetyl ether and stearyl ether (10 E.O.) | 5% by weight |
| Vaseline oil | 6% by weight |
| Isopropyl myristate | 3% by weight |
| Silicone oil | 1% by weight |
| Cetyl alcohol | 1% by weight |
| Antiseptic | proper amount |
| Perfume | proper amount |
| Water | balance |

EXAMPLE 14: Sun milk (milky lotion)

The following components were compounded and treated in the same way as Example 11 to prepare a sun milk.

| (A) | |
|---|---|
| 2-Ethylhexyl p-methoxy cinnamate | 2% by weight |
| 2-Ethylhexyl p-dimethyl amino benzoate | 2% by weight |
| Ethyl 4-(3,4-dimethoxy phenyl-methylene)-2,5-dioxo-1-imidazolidine-propionate | 1% by weight |
| Liquid paraffin | 22.6% by weight |
| Solid paraffin | 4.5% by weight |
| Cetanol | 4% by weight |
| Sorbitan monostearate | 1.8% by weight |
| Polyoxyethylene sorbitan mono-stearate (20 E.O.) | 2.8% by weight |
| Nδ-cocoyl ornithin | 5% by weight |
| (B) | |
| Triethanolamine pyrrolidone-carboxylate | 4% by weight |
| Water | 50.1% by weight |
| Antiseptic | 0.2% by weight |

EXAMPLE 15: Anti-sunburn lotion

The components (A) were dissolved under heating according to the following formulation and cooled to room temperature, and then the component (B) was added thereon to prepare an anti-sunburn lotion.

| (A) | |
|---|---|
| Iso-butyl p-methoxycinnamate | 1% by weight |
| Iso-butyl 4-(3,4-dimethoxy-phenyl methylene)-2,5-dioxo-1-imidazolidine propionate | 1% by weight |
| Glycerin | 5% by weight |
| Polyethylene glycol 400 | 0.5% by weight |
| Perfume | proper amount |
| Water | balance |
| (B) | |
| 96% ethanol | 40% by weight |

EXAMPLE 16: Lipstick

A lipstick was prepared according to the following formulation. A part of (B) was added to (A) and the mixture was subjected to rolling to prepare the pigment portion. Then the components of (B) dissolved by heating were added thereto and the mixture was homogenized, rapidly cooled for solidifying it, and then shaped.

| (A) | |
|---|---|
| Titanium dioxide | 2% by weight |
| 2-Ethylhexyl p-methoxycinnamate | 3.0% by weight |
| Ethyl 4-(3,4-dimethoxy phenyl-methylene)-2,5-dioxo-1-imidazolidinepropionate | 2.7% by weight |
| (B) | |
| Hexadecyl alcohol | 25% by weight |
| Lanolin | 4% by weight |
| Beeswax | 5% by weight |
| Ozocerite | 4% by weight |

| Candelilla wax | 7% by weight |
|---|---|
| Carnauba wax | 2% by weight |
| Antioxidant | proper amount |
| Perfume | proper amount |
| Castor oil | balance |

EXAMPLE 17: Oily sun gel

The fatty materials were dissolved by heating to 40° to 45° C. according to the following formulation, then silica was added thereto under stirring, and the mixture was cooled to prepare an oily sun gel.

| 2-Ethylhexyl p-methoxycinnamate | 2% by weight |
|---|---|
| 2-Ethylhexyl 4-(3,4-dimethoxy phenyl-methylene)-2,5-dioxo-1-imidazolidine-propionate | 3% by weight |
| Cacao fat | 2.5% by weight |
| Silica | 10% by weight |
| Antioxidant | proper amount |
| Perfume | proper amount |
| Fatty acid triglyceride ($C_8$–$C_{12}$) | balance |

EXAMPLE 18: Effervescent air spray 90 parts of a mixture of the following composition and 10 parts of Freon gas (F21/F114=40/60) were charged into a pressure vessel to make an effervescent air spray.

| n-Amyl p-dimethylamino-benzoate | 0.2% by weight |
|---|---|
| Diethyl 4-(3,4-dimethoxy phenyl methylene)-2,5-dioxo-1,3-imidazolidinedipropionate | 0.1% by weight |
| Stearic acid | 7% by weight |
| Propylene glycol | 7% by weight |
| Triethanolamine | 6% by weight |
| Olive oil | 2% by weight |
| Water | balance |

EXAMPLE 19: Non-effervescent lotion air spray 30 parts of a mixture of the following composition and 70 parts of Freon gas (F21/F114=40/60) were charged into a pressure vessel to make a non-effervescent lotion air spray.

| 2-Ethylhexyl p-dimethylamino-benzoate | 0.5% by weight |
|---|---|
| 2-Ethylhexyl 4-(3,4-dimethoxy phenylmethlene)-2,5-dioxo-1-imidazolidinepropionate | 0.5% by weight |
| Propylene glycol | 10% by weight |
| 99% ethanol | 30% by weight |
| Water | balance |

EXAMPLE 20: Foundation

The components (C) were mixed and dissolved by heating at 70° C. according to the following formulation (oil phase). Separately, the components (B) were mixed and dissolved and maintained at 70° C. (aqueous phase). The components (A) were dispersed in the aqueous phase, to which the oil phase was added and emulsified, and then the mixture was cooled to prepared a foundation.

| (A) | |
|---|---|
| 2-Ethylhexyl p-dimethylamino-benzoate | 3.0% by weight |
| 2-Ethylhexyl p-methoxycinnamate | 3.0% by weight |
| 2-Ethylhexyl 4-(3,4-dimethoxy-phenylmethylene)-2,5-dioxo-1-imidazolidinepropionate | 2.0% by weight |
| Diethyl 4-(3,4-dimethoxy phenyl-methlene)-2,5-dioxo-1,3-imidazolidine dipropionate | 2.0% by weight |
| Titanium oxide | 6% by weight |
| Red iron oxide | 1.5% by weight |
| Yellow iron oxide | 0.2% by weight |
| (B) | |
| Monomagnesium N-lauroylglutamate | 0.5% by weight |
| Triethanolamine | 1.4% by weight |
| Propylene glycol | 9.5% by weight |
| Water | 37.9% by weight |
| (C) | |
| Stearic acid | 2.8% by weight |
| Propylene glycol monostearate | 2.8% by weight |
| Glycerin monosterarate (Self-emulsifiable type) | 2.8% by weight |
| Liquid paraffin | 24.6% by weight |

EXAMPLE 21: Face powder

The materials were mixed according to the following formulation to obtain a face powder.

| 2-Ethylhexyl p-dimethylamino-benzoate | 5.0% by weight |
|---|---|
| 3,3,35-trimethylcyclohexyl salicylate | 2.0% by weight |
| 2-hydroxy-4-methoxy-benzophenone | 5.0% by weight |
| 2-Ethylhexyl 4-(3,4-dimethoxy phenylmethylene)-2,5-dioxo-1-imidazolidinepropionate | 1.0% by weight |
| Talc | 30% by weight |
| Titanium oxide | 15% by weight |
| Kaolin | 10% by weight |
| Nε-lauroyllysine | 5% by weight |
| Zinc laurate | 10% by weight |
| Iron oxide (red, yellow and black) | 5% by weight |
| Perfume | 3% by weight |

EXAMPLE 22: Rinse

The components (A) were mixed and dissolved by heating at 80° C. according to the following formulation, and then (B) was added and dispersed therein. To this dispersion was added (C) which had been dissolved at 80° C., and the solution was mixed and emulsified and then cooled to room temperature to prepare a rinse.

| (A) | |
|---|---|
| 2-Ethylhexyl p-dimethylamino-benzoate | 0.5% by weight |
| 2-Ethylhexyl 4-(3,4-dimethoxy phenylmethylene)-2,5-dioxo-1-imidazolidine propionate | 0.5% by weight |
| Dimethyl distearyl ammonium chloride | 1% by weight |
| $N^\alpha$-Cocoyl-Arginine ethyl ester | 0.5% by weight |
| Polyoxyethylene sorbital mono-oleate (4 E.O.) | 0.5% by weight |
| Polyoxyethylene sorbital monooleate (25 E.O.) | 0.5% by weight |
| Water | 80.5% by weight |
| (B) | |
| Nε-lauroyllysine | 2% by weight |
| (C) | |
| Liquid paraffin | 2% by weight |

| Cetanol | 3% by weight |
|---|---|

What is claimed is:

1. A sunburn-preventing cosmetic composition containing at least one UVB absorbing compound and at least one UVA absorbing compound in a weight ratio of 1:0.1–1:10, said at least one UVB absorbing compound being selected from the group consisting of p-dimethylaminobenzoic acid esters of the formula (I):

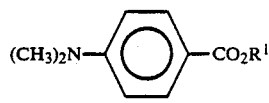

wherein $R^1$ is a $C_1$–$C_8$ linear alkyl group or a $C_3$–$C_8$ branched alkyl group and p-methoxycinnamic acid esters of the formula (II):

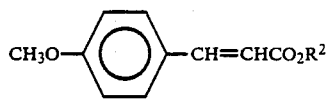

wherein $R^2$ is a $C_1$–$C_8$ linear alkyl group or a $C_3$–$C_8$ branched or cyclic alkyl group, and said at least one UVA absorbing compound being selected from the group consisting of benzylidene compounds of the formula (IV):

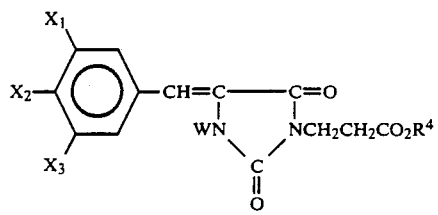

wherein $X_1$ and $X_3$ are independently a hydrogen atom or a methoxyl group, $X_2$ is a hydroxyl group or a methoxyl group, W is a hydrogen atom or a —$CH_2CH_2CO_2R_4$ group, and $R^4$ is a $C_1$–$C_{18}$ linear alkyl group or a $C_3$–$C_{18}$ branched or substituted or non-substituted cyclohexyl group.

2. The cosmetic composition of claim 1, wherein said at least one UVB absorbing compound and said at least one UVA absorbing compounds are present in said composition in an amount of 0.1 to 15% by weight and 0.01 to 15% by weight, respectively.

3. The cosmetic composition of claim 1 wherein said weight ratio is 1:0.5–1:5.

4. The cosmetic composition of claim 1 wherein said benzylidene compounds of the formula (IV) are those compounds of the formula (IV) wherein $X_1$ and $X^2$ are each a methoxyl group, $X^3$ is a hydrogen atom, W is a hydrogen atom or a —$CH_2CH_2CO_2R^4$ group, and $R^4$ is a methyl, ethyl, i-propyl, n-butyl, i-butyl, n-amyl, i-amyl, n-hexyl, cyclohexyl, n-octyl, 2-ethylhexyl, 2,2,4-trimethylcyclohexyl, decyl, lauryl, myristyl, cetyl or stearyl group.

5. The cosmetic composition of claim 1 wherein said benzylidene compounds of the formula (IV) are those compounds of the formula (IV) wherein $X_1$ and $X^2$ are each a methoxyl group, $X_3$ is a hydrogen atom, W is a hydrogen atom or a —$CH_2CH_2CO_2R^4$ group, and $R^4$ is a methyl, ethyl, n-butyl, i-butyl, or 2-ethylhexyl group.

6. The cosmetic composition of claim 1 wherein said benzylidene compounds of the formula (IV) are 2-ethylhexyl 4-(3,4-dimethoxyphenyl methylene)-2,5-dioxo-1-imidazolidinepropionate.

7. The cosmetic composition of claim 1 wherein said p-dimethylaminobenzoic acid esters of the formula (I) are those compounds of the formula (I) wherein $R^1$ is an ethyl, n-butyl, i-butyl, n-amyl, i-amyl, n-octyl or 2-ethylhexyl group.

8. The cosmetic composition of claim 1 wherein said p-dimethylaminobenzoic acid esters of the formula (I) are 2-ethylhexyl p-dimethylaminobenzoate.

9. The cosmetic composition of claim 1 wherein said p-methoxycinnamic acid esters of the formula (II) are those compound of the formula (II) wherein $R^2$ is an n-propyl, i-propyl, i-amyl, 2-ethylhexyl or cyclohexyl group.

10. The cosmetic composition of claim 1 wherein said p-methoxycinnamic acid esters of the formula (II) are 2ethylhexyl p-methoxycinnamate.

11. The cosmetic composition of claim 1 wherein said UVB absorbing compound is selected from the group consisting of 2-ethylhexyl p-dimethylaminobenzoate and 2-ethylhexyl p-methoxycinnamate and said UVA absorbing compound is 2-ethylhexyl 4-(3,4-dimethoxyphenyl methylene)-2,5-dioxo-1-imidazolidinepropionate.

12. A UV absorber comprising at least one UVB absorbing compound and at least one UVA absorbing compound in an weight ratio of 1:0.1–1:10, said at least one UVB absorbing compound being selected from the group consisting of p-dimethylaminobenzoic acid esters of the formula (I):

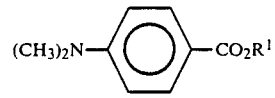

wherein $R^1$ is a $C_1$–$C_8$ linear alkyl group or a $C_3$–$C_8$ branched alkyl group and p-methoxycinnamic acid esters of the formula (II):

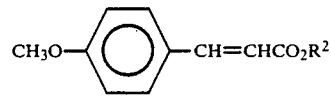

wherein $R^2$ is a $C_1$–$C_8$ linear alkyl group or a $C_3$–$C_8$ branched or cyclic alkyl group, and said at least one UVA absorbing compound being selected from the group consisting of benzylidene compounds of the formula (IV):

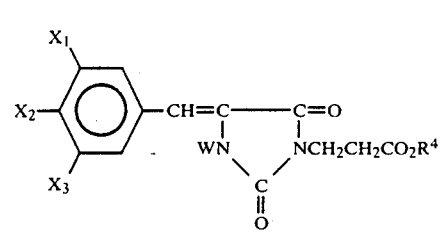

wherein $X_1$ and $X_3$ are independently a hydrogen atom or a methoxyl group, $X_2$ is a hydroxyl group or a methoxyl group, W is a hydrogen atom or a —$CH_2CH_2CO_2R^4$ group, and $R^4$ is a $C_1$–$C_{18}$ linear alkyl group or a $C_3$–$C_{18}$ branched or substituted or non-substituted cyclohexyl group.

13. The UV absorber of claim 12 wherein said weight ratio is 1:0.5–1:5.

14. The UV absorber of claim 11 wherein said benzylidene compounds of the formula (IV) are those compounds of the formula (IV) wherein $X_1$ and $X_2$ are each a methoxyl group, $X_3$ is a hydrogen atom, W is a hydrogen atom or a —$CH_2CH_2CO_2R^4$ group, and $R^4$ is a methyl, ethyl, i-propyl, n-butyl, i-butyl, n-amyl, i-amyl, n-hexyl, cyclohexyl, n-octyl, 2-ethylhexyl, 2,2,4-trimethylcyclohexyl, decyl, lauryl, myristyl, cetyl or stearyl group.

15. The UV absorber of claim 11 wherein said benzylidene compounds of the formula (IV) are those compounds of the formula (IV) wherein $X_1$ and $X_2$ are each a methoxyl group, $X_3$ is a hydrogen atom, W is a hydrogen atom or a —$CH_2CH_2CO_2R^4$ group, and $R^4$ is a methyl, ethyl, n-butyl, i-butyl, or 2-ethylhexyl group.

16. The UV absorber of claim 12 wherein said benzylidene compounds of the formula (IV) are 2-ethylhexyl 4-(3,4-dimethoxyphenyl methylene)-2,5-dioxo-1-imidazolidinepropionate.

17. The UV absorber of claim 12 wherein said p-dimethylaminobenzoic acid esters of the formula (I) are those compounds of the formula (I) wherein $R^1$ is an ethyl, n-butyl, i-butyl, n-amyl, i-amyl, n-octyl or 2-ethylhexyl group.

18. The UV absorber of claim 11 wherein said p-dimethylaminobenzoic acid esters of the formula (I) are 2-ethylhexyl p-dimethylaminobenzoate.

19. The UV absorber of claim 12 wherein said p-methoxycinnamic acid esters of the formula (II) are those compound of the formula (II) wherein $R^2$ is an n-propyl, i-propyl, i-amyl, 2-ethylhexyl or cyclohexyl group.

20. The UV absorber of claim 12 wherein said p-methoxycinnamic acid esters of the formula (II) are 2-ethylhexyl p-methoxycinnamate.

21. The UV absorber of claim 12 wherein said UVB absorbing compound is selected from the group consisting of 2-ethylhexyl p-dimethylaminobenzoate and 2-ethylhexyl p-methoxycinnamate and said UVA absorbing compound is 2-ethylhexyl 4-(3,4-dimethoxyphenyl methylene)-2,5-dioxo-1-imidazolidinepropionate.

* * * * *